US011417127B2

(12) United States Patent
Bordy et al.

(10) Patent No.: US 11,417,127 B2
(45) Date of Patent: Aug. 16, 2022

(54) METHOD FOR EARLY OBSERVATION OF COLONIES OF MICROORGANISMS

(71) Applicant: Commissariat A L'Energie Atomique et aux Energies Alternatives, Paris (FR)

(72) Inventors: Thomas Bordy, Grenoble (FR); Cedric Allier, Grenoble (FR); Pierre Marcoux, Grenoble (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 16/845,123

(22) Filed: Apr. 10, 2020

(65) Prior Publication Data

US 2020/0327306 A1 Oct. 15, 2020

(30) Foreign Application Priority Data

Apr. 12, 2019 (FR) .................................... 19 03964

(51) Int. Cl.

*G06K 9/00* (2022.01)
*G06V 20/69* (2022.01)
*G01N 21/47* (2006.01)

(52) U.S. Cl.

CPC ....... *G06V 20/693* (2022.01); *G01N 21/4788* (2013.01)

(58) Field of Classification Search

CPC ...................... G06K 9/00134; G01N 21/4788
USPC ........................................................ 348/79
See application file for complete search history.

(56) References Cited

U.S. PATENT DOCUMENTS 7,465,560 B2 * 12/2008 Hirleman, Jr .......... G01N 21/21 435/34
2003/0082516 A1 * 5/2003 Straus ................ G01N 15/1429 435/4
2006/0172370 A1 * 8/2006 Hirleman, Jr. ......... G01N 21/21 435/34

(Continued)

FOREIGN PATENT DOCUMENTS

FR 3054037 7/2013
WO WO 2018/215337 A1 11/2018

OTHER PUBLICATIONS

Yoshiaki Maeda et al. "Colony fingerprint for discrimination of microbial species based on lensless imaging of microcolonies." Division of Biotechnology and Life Science, Institute of Engineering, Tokyo University of Agriculture and Technology, Tokyo, Japan. Malcom Co., Tokyo, Japan. Apr. 3, 2017.

*Primary Examiner* — Joseph G Ustaris
*Assistant Examiner* — Jimmy S Lee
(74) *Attorney, Agent, or Firm* — Oblon, McClelland, Maier & Neustadt, L.L.P.

(57) ABSTRACT

A method for observation of a sample, the sample comprising microorganisms immersed in a nontransparent culture medium, the culture medium being favorable to the development of the microorganisms, and the sample being arranged between a light source and an image sensor, includes illuminating the sample with the light source, the light source emitting light propagating along an axis of propagation; acquiring an image of the sample by the image sensor; and, from the image acquired, characterizing the microorganisms. Light travels along the microorganisms through the culture medium to the sensor.

21 Claims, 8 Drawing Sheets

(56) References Cited

U.S. PATENT DOCUMENTS

| | | | | |
|---|---|---|---|---|
| 2012/0044340 | A1* | 2/2012 | Yamamoto | G02B 21/14 348/79 |
| 2012/0218379 | A1* | 8/2012 | Ozcan | G03H 1/0866 348/40 |
| 2013/0258091 | A1* | 10/2013 | Ozcan | G06K 9/0014 348/79 |
| 2018/0211095 | A1* | 7/2018 | Jalenques | C12Q 1/04 |
| 2018/0285624 | A1 | 10/2018 | Robinson et al. | |
| 2018/0299374 | A1* | 10/2018 | Holman | G01N 21/3563 |

* cited by examiner

METHOD FOR EARLY OBSERVATION OF COLONIES OF MICROORGANISMS

TECHNICAL FIELD

The technical field of the invention is the observation of colonies of microorganisms, and in particular colonies developing in a nontransparent culture medium.

PRIOR ART

Observation of bacterial colonies by imaging is a technique that has been known for a long time in the field of microbiology, for monitoring the development of microorganisms or cells. It is possible to monitor the development of colonies, for example bacterial colonies, and count them, in a Petri dish. The form of the colonies provides information on the type of microorganism. Furthermore, by combining the use of different culture media, which either allow or do not allow colonies to develop, it is possible to identify the type of colony-forming microorganism.

Characterization of microorganisms on Petri dishes is still a reference method, often used in the field of microbiology, diagnostics, but also in the field of agriculture and food production or cosmetics. The main drawback of this method is that it is slow, since it is generally necessary to wait several days to obtain a usable result. Another drawback is that this method is difficult to automate, and requires experienced human operators.

Recently, holographic methods have made it possible to count and characterize microorganisms, and they represent promising alternatives to the existing techniques, allowing better automation. For example, U.S. Pat. No. 7,465,560 describes a method for characterizing a microorganism based on the exploitation of diffusion and diffraction of an incident laser beam by the microorganism. The microorganism is arranged between a laser light source and an image sensor. Under the effect of illumination by the laser beam, an image is acquired on which diffraction patterns appear, the latter constituting a signature of the microorganism observed. U.S. Pat. No. 8,787,633 describes a method having the same objective.

Moreover, the work by Meada Y. “Colony fingerprint for discrimination of microbial species based on lensless imaging of microcolonies”, PLoS ONE 12(4) (2017), describes a method for observation of bacterial colonies according to a lensless imaging configuration. The colonies develop in LB Agar (Lysogeny Broth Agar) with a thickness of 600 μm. This agar is transparent, which allows correct observation of the colonies.

However, the holographic methods described above become inapplicable if the medium in which the microorganisms are disposed is opaque, colored or diffusing. In fact, these methods use an image formed according to a so-called transmission configuration, in which the sample is arranged between a light source and an image sensor. Obtaining a usable image is subject to the use of a sufficiently transparent sample. Thus, this method is not compatible with samples comprising a colored and/or diffusing culture medium, for example the medium known by the acronym COS (Columbia Sheep Blood) comprising a Columbia agar with sheep blood. It is also not applicable to an opaque, diffusing medium of the chocolate agar type. Now, culture media of this kind are often used in clinical diagnostics.

The documents WO2018122504 and WO2018122505 describe a method of bacterial identification according to a backscattering configuration: a light source illuminates a colony and an image sensor acquires an image based on radiation reflected by the bacterial colony. This method is very suitable for identifying colonies, but it does not allow efficient counting of the colonies distributed in a sample, except by scanning the sample.

The inventors have designed a particularly quick optical method for counting colonies of microorganisms, allowing early characterization of samples.

DISCLOSURE OF THE INVENTION

The invention relates to a method for observation of a sample, the sample comprising microorganisms immersed in a nontransparent culture medium, the culture medium being favorable to the development of the microorganisms, the sample being arranged between a light source and an image sensor, the method comprising:

a) illuminating the sample with the light source, the light source emitting an incident light wave propagating along an axis of propagation;

b) acquiring an image of the sample by the image sensor; and c) from the image acquired, detecting the microorganisms;

the method being characterized in that the culture medium extends, parallel to the axis of propagation, to a thickness of less than 500 μm.

The culture medium may extend, parallel to the axis of propagation, to a thickness of less than 250 μm or less than 100 μm.

According to one embodiment, the culture medium extends between an upper face and a lower face, perpendicular or approximately perpendicular to the axis of propagation. As they develop, the microorganisms form colonies, at least one colony forming a light channel extending from the upper face to the lower face, through the culture medium, in such a way that at least one colony forms a light spot on the image acquired by the image sensor. According to this embodiment, the method may comprise:

- counting light spots formed on the image acquired by the image sensor; and
- estimating the number of colonies in the sample, as a function of the number of light spots counted on the image.

“Light spot” means a point zone, comprising for example some tens or some hundreds of pixels, whose intensity is greater than that of the pixels adjacent to the point zone.

The method may comprise:

- performing a morphological analysis of at least one light spot formed on the image acquired by the image sensor; and
- identifying the colony that produced the light spot, based on the morphological analysis.

“Identification of a colony” means determination of the species of microorganisms forming the colony.

According to one embodiment, the image acquired comprises at least one diffraction pattern, associated with a colony of microorganisms. The method then comprises:

- counting each diffraction pattern, so as to estimate a quantity of colonies in the sample;
- and/or morphological analysis of at least one diffraction pattern, as well as identification of the colony associated with the diffraction pattern, based on the morphological analysis.

According to one embodiment, the method comprises:

- employing a neural network, based on the image acquired, for detecting the diffraction patterns; and counting the diffraction patterns thus detected.

The neural network may have been parameterized beforehand in a learning phase, using samples comprising microorganisms whose position is known, and whose species is preferably known.

According to one embodiment, the method comprises:

acquisition of a first image, at a first time point, the image comprising at least one diffraction pattern associated with a colony of microorganisms; and acquisition of a second image, at a second time point, subsequent to the first time point, the second image comprising at least one light spot associated with the colony of microorganisms.

According to one embodiment:

the culture medium extends in a confinement chamber;

the culture medium extends between two opposite faces, perpendicular or approximately perpendicular to the axis of propagation: and the confinement chamber is in contact with the culture medium at the level of the two opposite faces.

According to one embodiment, no image forming lens is arranged between the sample and the image sensor.

According to one embodiment, an image-forming optical system is arranged between the sample and the image sensor, the optical system defining an object plane and an image plane; and the image sensor defines a detection plane;

the method being such that during image acquisition:

the sample is displaced relative to the object plane by an object defocusing distance;

and/or the detection plane is displaced, relative to the image plane, by an image defocusing distance.

"Image-forming optical system" means an objective or a lens.

According to one embodiment, an image-forming optical system is arranged between the sample and the image sensor, the optical system defining an object plane and an image plane; and the image sensor defines a detection plane;

the method being such that during image acquisition the lower face of the sample corresponds to the object plane and the detection plane corresponds to the image plane.

The invention will be better understood on reading the account of embodiment examples presented hereunder in conjunction with the figures listed below.

FIGURES

DESCRIPTION OF PARTICULAR EMBODIMENTS

Figure 1A:
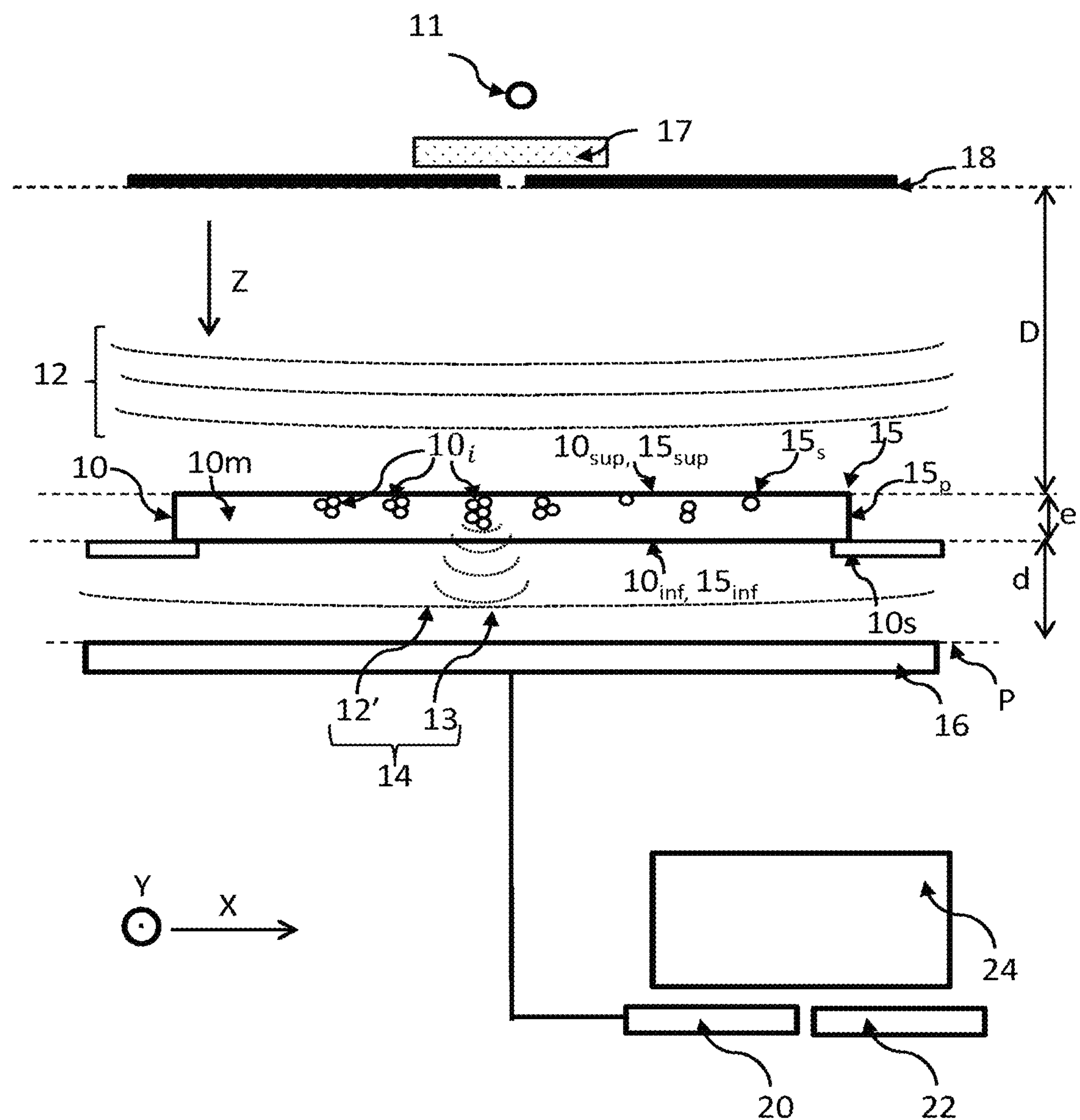
FIGS. 1A and 1B show an example of a device for implementing the invention, according to a lensless imaging configuration.
Figure 1B:
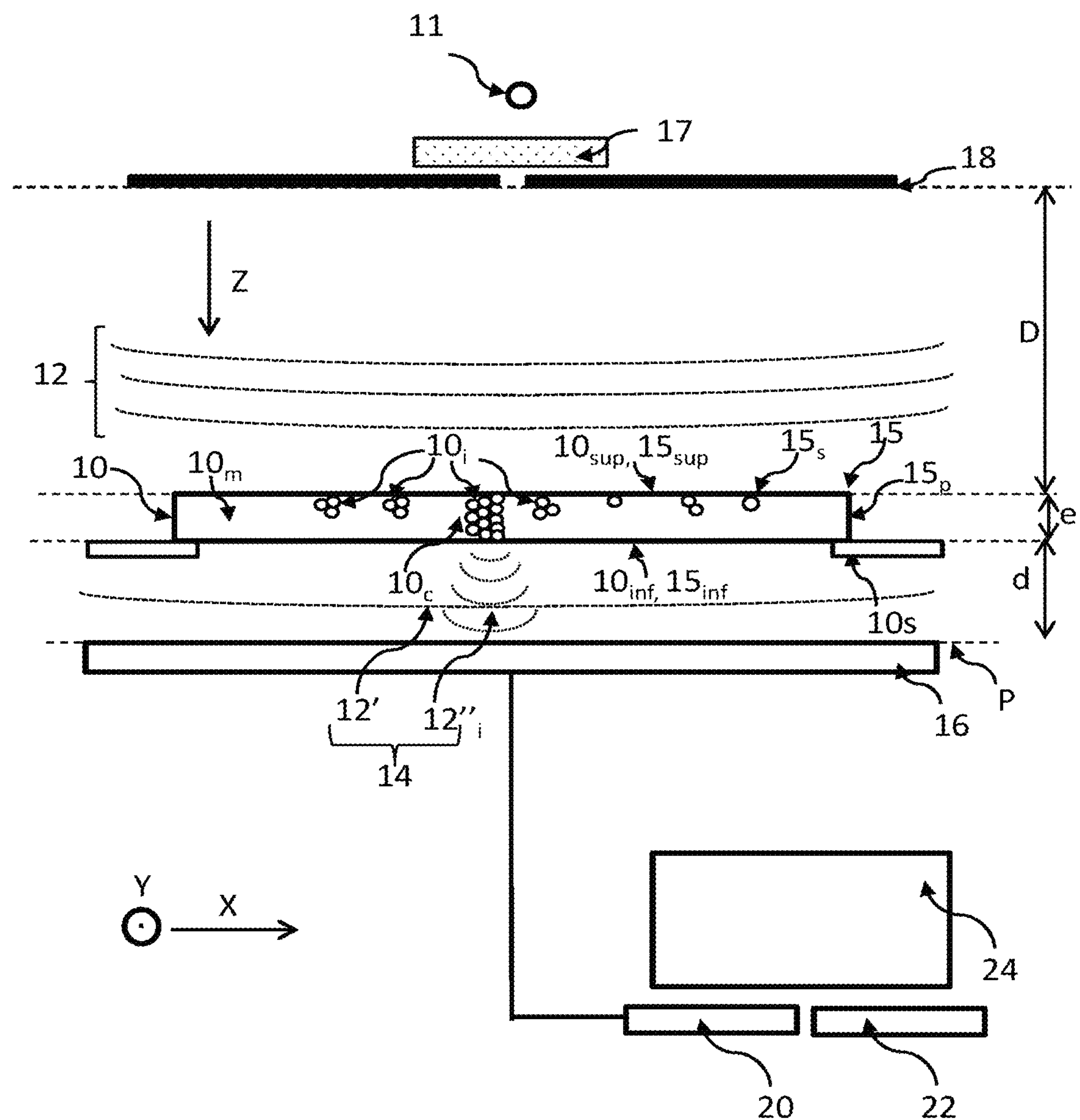

FIGS. 1A and 1B show an example of a device for applying a method according to the invention. A light source 11 is configured for emitting a light wave 12, called incident light wave, propagating in the direction of a sample 10, along an axis of propagation Z. The light wave is emitted according to an illumination spectral band Δλ.

The sample 10 comprises microorganisms $\mathbf{10}_i$ that we wish to detect, in order to count them or characterize them, for example identifying them. The microorganisms are immersed in a medium $\mathbf{10}_m$, forming a culture medium that is favorable to the development of the microorganisms, and in particular to colonies of microorganisms. The medium $\mathbf{10}_m$ comprises nutrients allowing development of the microorganisms. "Microorganism" means notably a yeast, a bacterium, a spore, a fungus or a cell, whether it is a eukaryotic or a prokaryotic cell, or a microalga.

The method does not require microorganisms staining, such as viability staining. In a preferred embodiment, the sample does not comprise a viability stain.

When the microorganisms form colonies, the concentration may for example be less than 1000 colonies of microorganisms per $mm^2$. The sample is confined in a confinement chamber 15. The latter is held, between the light source 11 and an image sensor 16, by a sample holder 10*s*.

The distance D between the light source 11 and the confinement chamber 15 is preferably greater than 1 cm. It is preferably between 2 and 30 cm. Advantageously, the light source, viewed by the sample, is considered to be a point source. This signifies that its diameter (or its diagonal) is preferably less than a tenth, better still less than a hundredth of the distance between the confinement chamber 15 and the light source. In FIGS. 1A and 1B, the light source 11 is a light-emitting diode. It is generally combined with a diaphragm 18, or spatial filter. The aperture of the diaphragm is typically between 5 μm and 1 mm, preferably between 50 μm and 500 μm. In this example, the diaphragm is supplied by Thorlabs under reference P150S and its diameter is 150 μm. The diaphragm may be replaced with an optical fiber, a first end of which is placed facing the light source 11 and a second end is placed opposite the sample 10. The device shown in FIGS. 1A and 1B also comprises a diffuser 17, arranged between the light source 11 and the diaphragm 18. The use of said diffuser makes it possible to overcome constraints on centering of the light source 11 relative to the aperture of the diaphragm 18. The function of said diffuser is to distribute the light beam produced by a unit light source 11 according to a cone of angle α. Preferably, the diffusion angle α varies between 10° and 80°. The use of a diffuser is described in WO2016078946. Alternatively, the light source may be a laser source, such a laser diode. In this case, it is not useful to combine it with a spatial filter or a diffuser.

Preferably, the emission spectral band Δλ of the incident light wave 12 has a width less than 100 nm. "Spectral band width" means the full width at half maximum of said spectral band.

The sample 10 is arranged between the light source 11 and the aforementioned image sensor 16. The latter extends preferably parallel, or approximately parallel to a plane over which the sample extends. The term "approximately parallel" signifies that the two elements need not be strictly parallel, an angular tolerance of some degrees, less than 20° or 10° being allowed. In this example, the sample extends over a plane XY, perpendicular to the axis of propagation Z.

The sample extends between an upper face $10_{sup}$, located opposite the light source 11, and a lower face $10_{inf}$, located opposite the image sensor 16. The upper and lower faces preferably extend perpendicularly or sensibly perpendicularly to the axis of propagation Z of the incident light wave 12. "Sensibly perpendicularly" means perpendicular, allowing an angular tolerance of ±20° or ±10°.

The image sensor 16 is able to form an image I of the sample 10 on a detection plane P. In the example shown, it is an image sensor comprising a pixel matrix, of the CCD type or a CMOS. The detection plane P preferably extends perpendicularly to the axis of propagation Z of the incident light wave 12.

The image sensor 16 is connected to a processing unit 20, configured for processing the images obtained by the image sensor. The processing unit 20 is connected to a memory 22, configured to allow the execution of operations of image processing. In this example, the processing unit 20 is also connected to a screen 24.

In the configuration shown in FIGS. 1A and 1B, it will be noted that there is no magnifying or image-forming lens between the image sensor 16 and the sample 10. This does not preclude the optional presence of focusing microlenses at the level of each pixel of the image sensor 16, these latter not having the function of magnifying the image acquired by the image sensor, their function being to optimize the efficacy of detection. In such a configuration, called lensless imaging, the distance d between the sample 10 and the pixel matrix of the image sensor 16 is preferably between 50 μm and 2 cm, preferably between 100 μm and 2 mm.

Figure 1C:
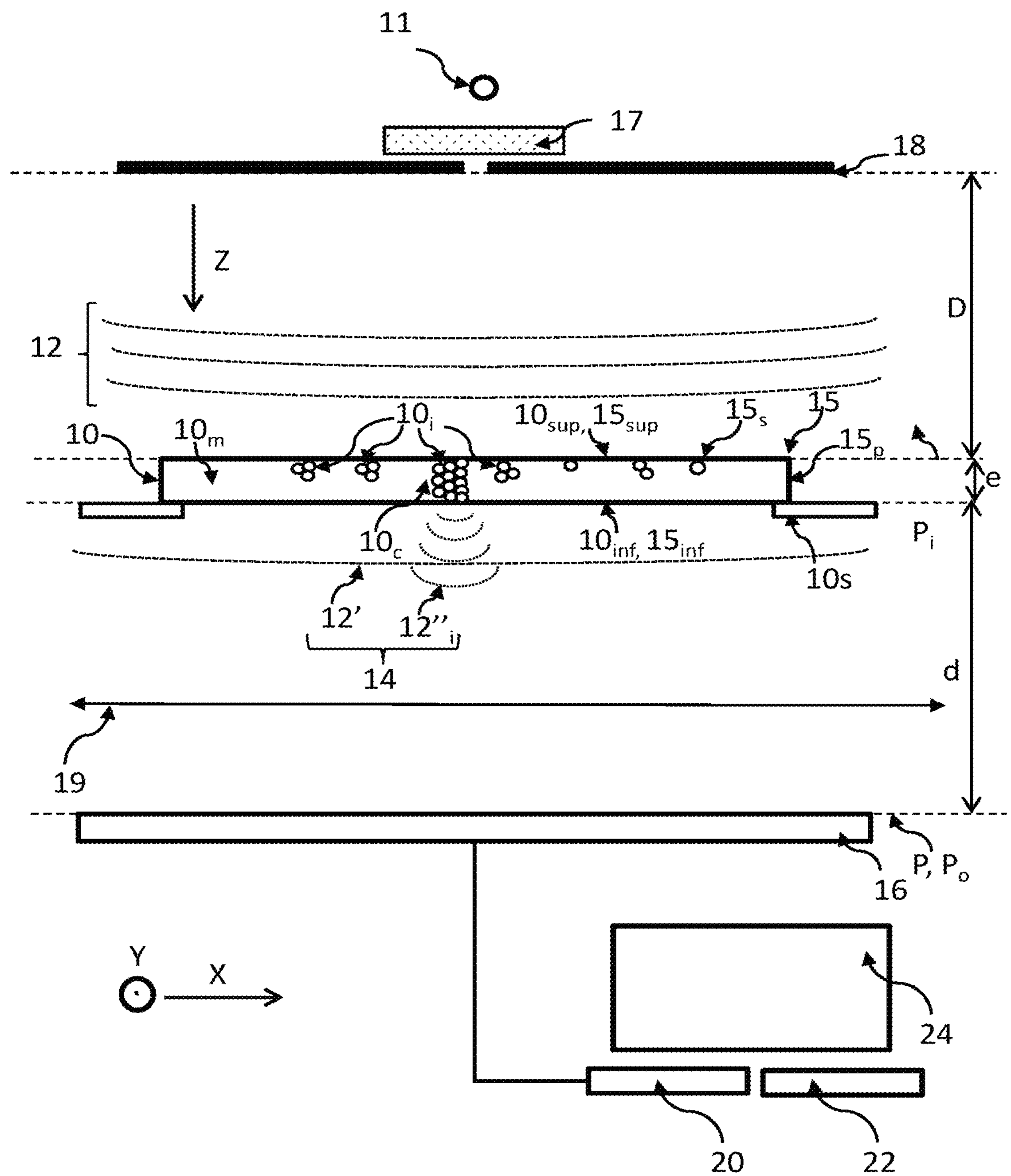
FIG. 1C shows a device of the invention in which an optical system extends between the sample and the image sensor.

In another configuration, an image-forming optical system 19 may be arranged between the sample and the image sensor, as shown in FIG. 1C. In this configuration, the optical system may be an objective and a lens. The optical system 19 defines an object plane $P_o$ and an image plane $P_i$. The object plane is preferably located in the sample, and in particular at the level of the lower face $10_{inf}$ of the sample. The image plane $P_i$ preferably coincides with the detection plane P. In order to allow observation of a large area of the sample, the magnification conferred by the optical system 19 is preferably equal to 1, or less than 1. When, however, observation of details of the sample is preferred, the magnification of the optical system 19 may be greater than 1. The configuration shown in FIG. 1C is a focused configuration, the optical system conjugating the sample, and preferably the lower face $10_i$, to the image sensor 16.

Figure 3A:
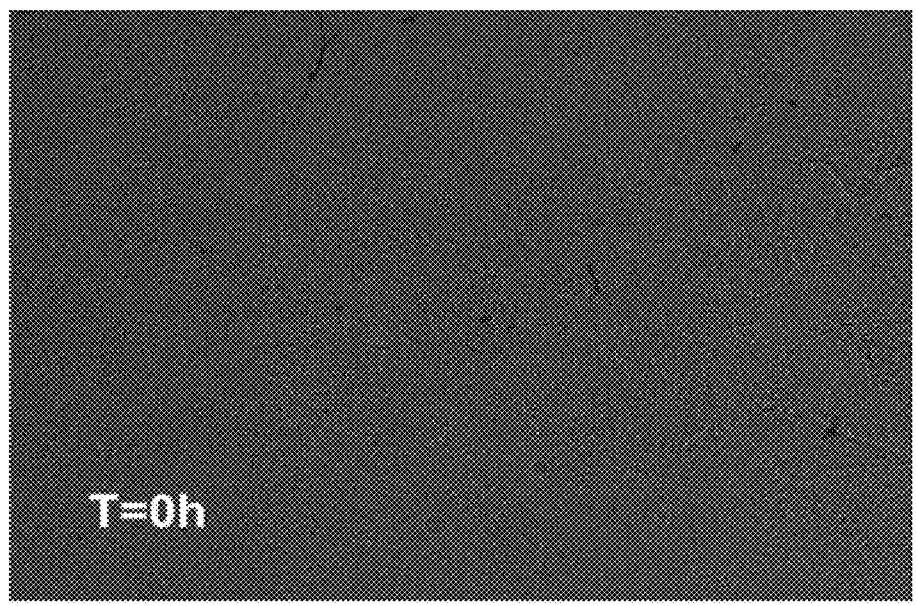
FIGS. 3A and 3B show images of a sample acquired at an initial time point and 4 hours after the initial time point, respectively.
Figure 3B:
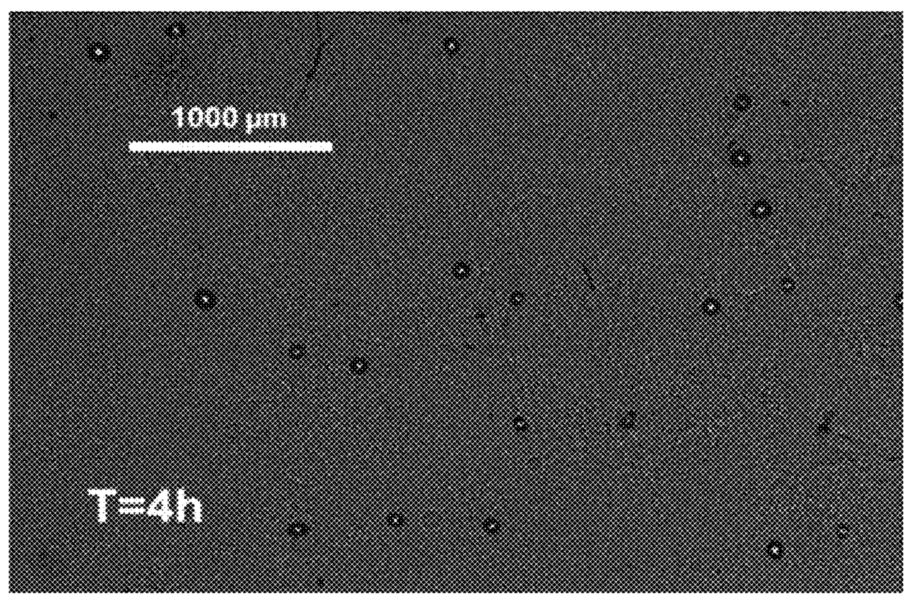

The advantage of the focused configuration is explained in conjunction with FIG. 3B.

According to another configuration, called defocused:

- the object plane $P_o$ is defocused relative to the sample, by an object defocusing distance;
- and/or the image plane $P_i$ is defocused relative to the detection plane formed by the image sensor, by an image defocusing distance.

The image defocusing distance and/or the object defocusing distance are preferably less than 1 mm, or even less than 500 μm.

Figure 2:
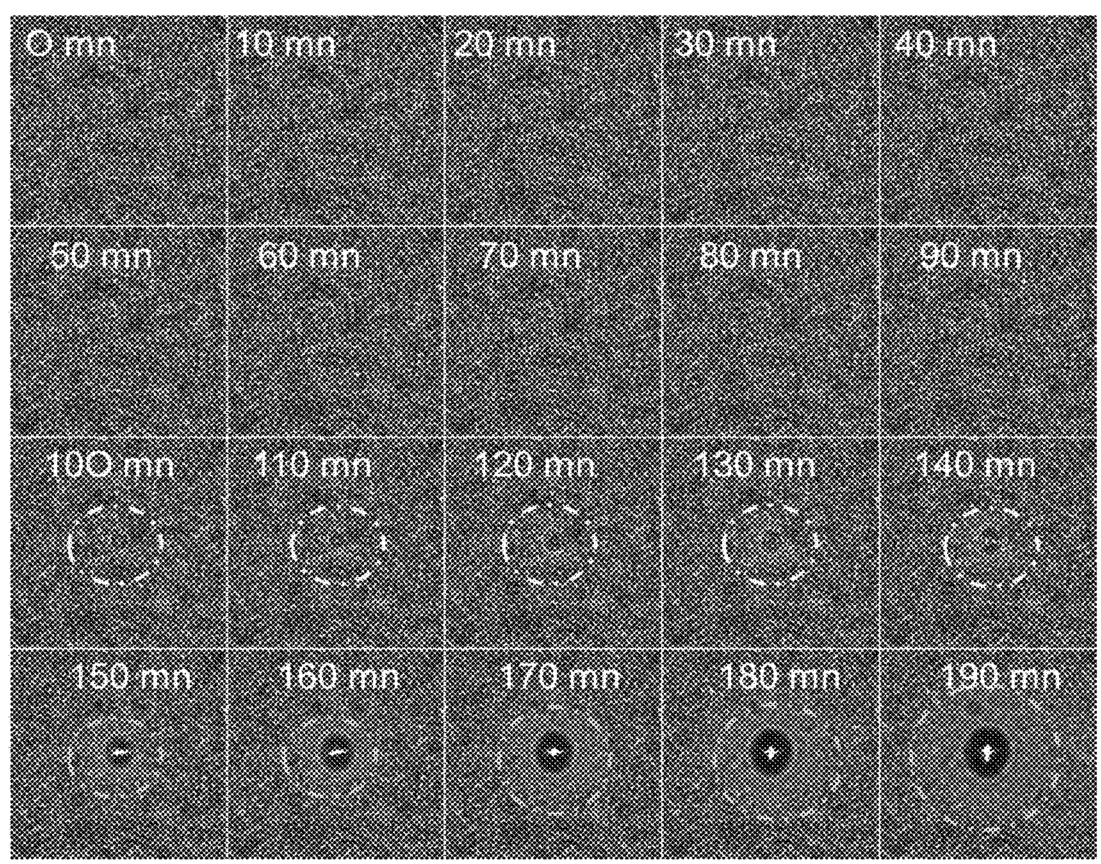
FIG. 2 shows parts of images of a sample acquired at different time points after an initial time point.

The advantage of a defocused configuration is explained in conjunction with FIG. 2.

The culture medium is a liquid medium or an agar medium commonly used in microbiology. For example, but not limiting, the culture medium may be:

- a Chapman medium, favorable to the development of halophilic and halotolerant microorganisms, for example, or bacteria of the types *Staphylococcus*, or *Micrococcus*, or *Enterococcus*, or *Bacillus;*
- a Hektoen medium, favorable to the development of *Salmonellae* or *Shigellae;*
- a *Salmonella-Shigella* agar, favorable to the isolation of pathogenic enterobacteria;
- an Eosin Methylene Blue (EMB) medium, favorable to the development of Gram-negative bacteria;
- a MacConkey medium, favorable to the development of Gram-negative bacilli, coliform bacteria, or of *Salmonella Shigella;*
- a CLED (Cystine Lactose Electrolyte Deficient) medium, commonly used in the study of bacteria present in urine, both Gram+ and Gram−;
- a BCP (Bromocresol Purple) medium, commonly used for detecting and isolating enterobacteria;
- a Baird Parker medium, favorable to the identification of bacteria of the *Staphylococcus aureus* type;
- a BEA (Bile Esculin Agar) medium, favorable to the identification of bacteria of the *Streptococcus* type;
- a blood agar (Columbia), favorable to the development of bacteria of the *Streptococcus* type;
- a cooked blood agar (chocolate);
- a kaolin agar;
- a Slanetz agar, usual for identifying bacteria of the *Enterococcus* type;
- a cetrimide agar, allowing isolation of bacteria of the *Pseudomonas* type;
- a Sabouraud agar, for isolating and identifying saprophytic or pathogenic yeasts or molds;
- a CIN (Cefsulodin Irgasan Novobiocin) agar, allowing isolation of bacteria of the *Yersinia enterocolitica* type;
- a milk agar;
- a starch agar;
- an egg agar;
- a Mossel agar;
- a Drigalski agar;
- a TSN (Tryptone Sulfite Neomycin) agar;
- a TCBS (Thiosulfate-citrate-bile salt-sucrose) agar;
- a lactose agar with deoxycholate;
- a Muller Hinton medium;
- an ordinary nutrient agar (Trypticase Soy Agar for example);
- a Todd Hewitt medium;
- a TTC (Triphenyl Tetrazolium Chloride) tergitol medium;
- a Hajna-Kligler medium;
- a Lysine Iron medium;
- a meat-liver medium;
- a Falkow medium;
- a Möller medium;
- a King medium A or a King medium B;
- a Rappaport medium;
- an Esculin agar;
- a Lowenstein-Jensen agar;
- a BLBVB broth ("bouillon lactosé bilié au vert brilliant"): brilliant green bile lactose broth.

This is not an exhaustive list.

The microorganisms may be seeded in the culture medium at a depth or on the surface.

Most of the media used in clinical microbiology are nontransparent. When they are used in conventional Petri dishes, their thickness is of the order of 5 mm, which makes them opaque. Owing to their opacity, as indicated in connection with the prior art, it is not conceivable to acquire a usable image of a sample according to the configurations shown in FIGS. 1A to 1C. Thus, an important element of the invention is that the thickness e of the sample, defined parallel to the axis of propagation Z, is far less than in the methods of the prior art. The thickness of the sample corresponds to the thickness of the culture medium 10$_m$. It is less than 1 mm, and preferably less than 500 μm, and more preferably less than 250 μm, or even less than 100 μm. The thickness e is generally above 10 or 20 μm. At this thickness, the culture medium 10$_m$ becomes translucent. “Translucent” means that it allows propagation of light through its thickness, without being transparent. Relative to the prior art, the reduction in thickness e makes it possible to form an image of the sample according to a transmission configuration, the sample extending between the light source 11 and the image sensor 16.

It should be noted that the reduction in thickness of the culture medium 10$_m$ is far from obvious. In fact, the methods of observation and counting of the prior art assume that the colonies have acquired a certain level of development, which assumes a certain length of time between seeding the culture medium and observing the bacterial colonies. This time is generally more than 1 day, or even more than several days. This justifies the use of a sufficiently thick culture medium, so as to contain an amount of nutrients necessary for proliferation of the microorganisms. On reducing the thickness of the culture medium, the methods of the prior art would not be usable, as the amount of nutrients stored in the culture medium would not allow a sufficient culture time.

The inventors have shown that by reducing the thickness of the culture medium, images can be formed in transmission. These images are usable and allow observation of the colonies at an early stage of development. Because of this, the culture time can be limited to a few hours, making it unnecessary to use a thick culture medium. The amount of nutrient necessary for the development of the colonies, prior to their characterization, is thus considerably reduced relative to the techniques of the prior art. Examples of observation of colonies are presented in conjunction with FIGS. 2, 3A and 3B.

The sample 10 is, in this example, contained in a confinement chamber 15. The confinement chamber 15 is preferably transparent. It comprises an upper wall 15$_{sup}$, a lower wall 15$_{inf}$ and a peripheral wall 15$_p$. The peripheral wall 15$_p$ extends between the upper wall 15$_{sup}$ and the lower wall 15$_{inf}$. Preferably, the peripheral wall is an annular wall extending around the axis of propagation Z. The lower wall 15$_{inf}$ and upper wall 15$_{sup}$ are preferably perpendicular, or approximately perpendicular, to the axis of propagation Z. The upper wall 15$_{sup}$ and lower wall 15$_{inf}$ are preferably arranged in contact with the upper 10$_{sup}$ and lower 10$_{inf}$ faces of the sample 10, respectively. The culture medium 10$_m$ may comprise a certain content of dissolved oxygen, which allows, to a certain extent, development by the aerobic route.

Confinement of the sample by the lower and upper walls makes it possible to keep the sample isolated relative to the environment, which limits the risks of contamination of the environment or of the sample.

FIG. 2 shows images acquired by the image sensor using a device according to a lensless imaging configuration, as shown in FIGS. 1A and 1B. We used a sample comprising a culture medium 10$_m$ of the horse blood agar type, obtained by mixing defibrinated horse blood with a TSA agar melted at 55° C. (trypticase soy agar supplied by VWR), the volume fraction of blood added being 5%, or 3 mL to 60 mL of TSA agar. The agar was seeded with a 600 μL solution containing bacteria of the *Escherichia coli* type at a concentration of 950 CFU (Colony Forming Units)/mL. Seeding took place while the agar was still liquid. The seeded agar was poured into a Geneframe chamber with thickness varying between 250 μm and 500 μm.

The other test parameters were as follows:

- image sensor: CMOS monochrome—pixel size 1.67 μm—active surface 30 mm$^2$;
- light source: four-quadrant LED, CREE MCE-Color;
- light source—image sensor distance: 5 cm;
- sample—image sensor distance: 1 mm;
- diffuser: Luminit 40°; and
- diaphragm: Thorlabs 150 μm.

The light source comprises quadrants emitting in a red (635 nm), green (520 nm) and blue (435 nm) illumination spectral band, respectively. The illumination spectral bands were used separately.

The sample was illuminated by means of the light source, in the 520 nm spectral band. An image of the sample was acquired every 10 minutes, using the image sensor. FIG. 2 shows one and the same region of interest of 20 images acquired successively between t=0 min and t=190 min. The time point t=0 min corresponds to an initial time point, considered to coincide with the pouring of the agar into the confinement chamber 15.

Between t=100 min and t=140 min, formation of a diffraction pattern is observed at the center of each image. The diffraction pattern is difficult to distinguish at t=100 min and becomes more and more discernible, in particular at t=130 min and t=140 min. The diffraction pattern is formed by interference between:

- a part 12' of the illumination light wave 12 emitted by the light source, the part 12' corresponding to the part of the light wave transmitted by the sample, i.e. not absorbed by the latter; and
- a diffraction wave 13, generated by a bacterial colony. The diffraction wave becomes more and more visible as the volume of the bacterial colony develops.

The superposition of the transmitted part 12' of the illumination light wave, and of the diffraction wave 13, forms an exposure light wave 14 propagating to the image sensor, and allowing detection of the colony. An exposure light wave of this kind is shown in FIG. 1A. A diffraction pattern generally has a central spot, around which concentric rings extend.

Detection, on the image formed by the image sensor, of these diffraction patterns makes it possible to detect development of bacterial colonies, and perform a count of the latter, at a particularly early stage of development. In fact, each colony may be associated with a diffraction pattern. Furthermore, the morphology of the diffraction pattern may allow identification of each colony. In fact, the morphology of the diffraction patterns depends on the type of microorganism forming the colony, as described in the prior art. Thus, the presence of diffraction patterns on the image acquired by the image sensor makes it possible to obtain qualitative and quantitative information at a very early stage of development, for example less than 2 hours after seeding.

The diffraction patterns, as described above, may also be observed according to a defocused configuration, as described above. The defocusing distance is then preferably less than 1 mm, or less than 500 μm, or even less than 200 μm or 100 μm.

When the colony develops, a remarkable phenomenon occurs, as can be seen on the thumbnails corresponding to the time points between t=150 min to 190 min. In fact, formation of intense light points is observed on the image acquired by the image sensor. These intense point zones are well delimited, and make it possible to perform particularly easy detection and counting of the colonies. The inventors explain the presence of the intense point zones by the development of the colonies, as shown in FIG. 1B. Owing to the small thickness of the culture medium, the bacterial colonies, as they develop, extend from the upper face $\mathbf{10}_{sup}$ of the sample to the lower face $\mathbf{10}_{inf}$ of the latter. They then form a channel $\mathbf{10}_c$ extending through the culture medium $\mathbf{10}_m$, the channel joining the upper face $\mathbf{10}_{sup}$ to the lower face $\mathbf{10}_{inf}$. The channel $\mathbf{10}_c$ forms a light guide, allowing easy propagation of a part $\mathbf{12}''_i$ of the incident light wave, propagating locally at the level of a colony $\mathbf{10}_i$ through the light guide formed by the channel $\mathbf{10}_c$.

Thus, after a certain stage of development of the colonies, the exposure light wave 14, arriving at the image sensor 16, comprises:

- a first part 12' of the illumination light wave 12 transmitted by the agar forming the sample: and
- a second part $\mathbf{12}''_i$ of the illumination light wave 12, transmitted locally by each channel $\mathbf{10}_c$, at the level of colonies $\mathbf{10}_i$, and forming intense point zones on the image, or light spots.

This results in formation of a particularly contrasted image, or each colony forms an intense spot on the image. This allows particularly easy detection and counting of the colonies formed in the sample.

FIGS. 3A and 3B show examples of images of the sample described above, formed at t=min (time point considered as corresponding to pouring of the agar into the sample) and at t=4 h, respectively. The image formed at t=4 h is sufficiently contrasted to count the colonies.

Thus the method allows:

- at a very early stage, formation of diffraction patterns, evidence of the presence of bacterial colonies in the agar, and allowing a first count, or even identification of the microorganisms forming each colony. By comparing two images acquired at two different time points, separated by an interval of at least ½ generation time, it is possible to distinguish the diffraction patterns obtained from growing microcolonies, from diffraction patterns obtained from sterile nonbiological objects that may be found conventionally in agar media (dust, precipitates), and
- at an early stage, i.e. in a few hours, typically in less than 6 h, formation of a contrasted image, formed by point light spots, each point light spot corresponding to a colony. This allows easy, reliable counting of the colonies. It is considered that the shape of the spots may depend on the type of microorganism. Thus, a morphological analysis of the image may allow qualitative information to be obtained, relating to the type of microorganism developing in the culture medium.

FIGS. 3A and 3B were acquired with a lensless configuration, as described in FIGS. 1A and 1B. Similar images, or even with higher contrast and higher resolution, may be obtained with an optical system 19 as described in FIG. 1C, according to a focused configuration. In this case, the object plane $P_o$ of the optical system 19 merges with the lower face $\mathbf{10}_{inf}$ of the sample, whereas the image plane $P_i$ of the optical system 19 merges with the detection plane P.

Figure 4:
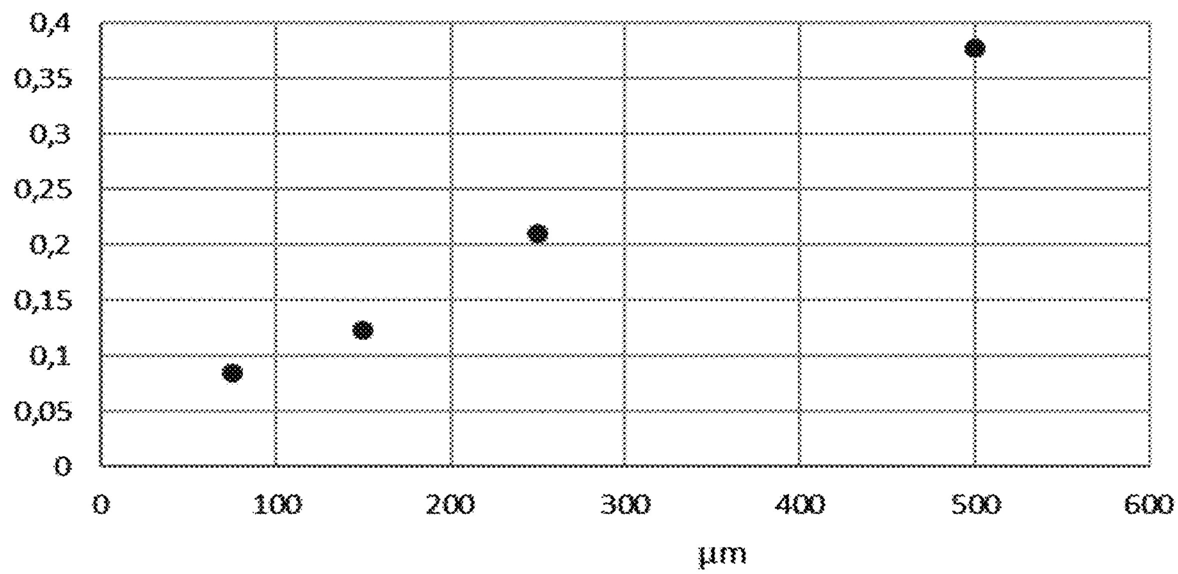
FIG. 4 shows the variation of the optical attenuation of an agar as a function of its thickness.

FIG. 4 shows the evolution of the light attenuation of the blood agar described above, as a function of the thickness. This figure was obtained using an unseeded blood agar, varying in thickness between 75 μm and 500 μm. The attenuation formed by the agar was evaluated relative to measurement of luminous intensity $I_o$ without agar between the light source and the image sensor.

The attenuation $Att_e$, corresponding to the thickness e, is obtained from the following expression, derived from the Beer Lambert law:

$$Att_e = -\ln\left(\frac{I_e}{I_0}\right) \quad (1)$$

where $I_e$ is the luminous intensity measured in the presence of a thickness e of agar.

The measurements shown in FIG. 4 were carried out at a wavelength of 540 nm.

Comparative measurements were undertaken using clear agar, of the TSA type. The attenuation shows little dependence on the thickness, and remains close to 0.05, for thicknesses between 100 and 500 μm.

The invention may be carried out provided that the attenuation, as defined in connection with equation (1), is below 0.5, and preferably below 0.4 or even 0.3.

The inventors consider that the method allows detection and counting of colonies whose diameter is between 5 μm and 50 μm, or more. The method allows particularly early detection of the colonies.

Figure 5A:
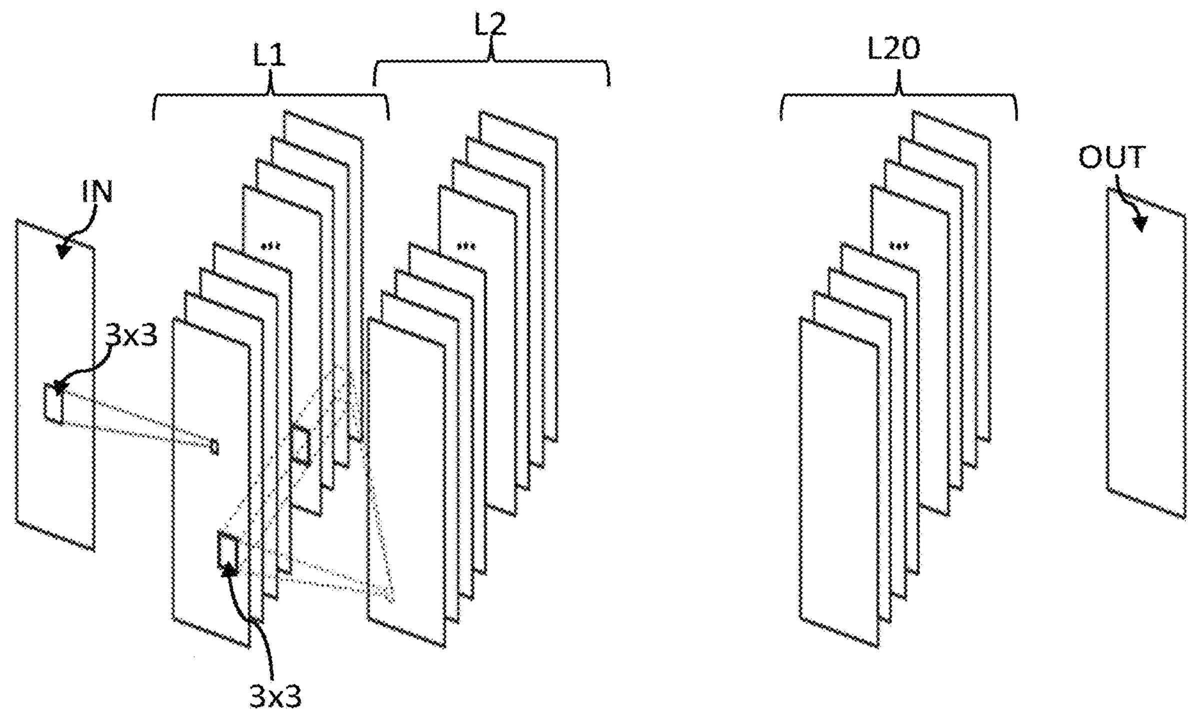
FIG. 5A shows schematically an architecture of a convolutional neural network.

According to one embodiment, counting of diffraction patterns, such as those shown in FIG. 2, is carried out using an automatic recognition algorithm, of the neural network type. More precisely, the algorithm is able to employ a convolutional neural network. The neural network comprises an input layer IN, formed from an image acquired by the image sensor, and an output layer OUT, corresponding to an image on which the colonies of microorganisms are detected. Between the input layer IN and the output layer OUT, the neural network comprises 20 layers L1, L2 . . . L20, with ranks between 1 (layer adjacent to the layer IN) and 20 (layer adjacent to the layer OUT). Each layer comprises 32 planes. A layer is obtained by convolution of the 32 planes of the layer of preceding rank by a convolution kernel of size 3×3. The layer IN is regarded as the layer of rank 0. FIG. 5A shows schematically an architecture of such a network.

Figure 5B:
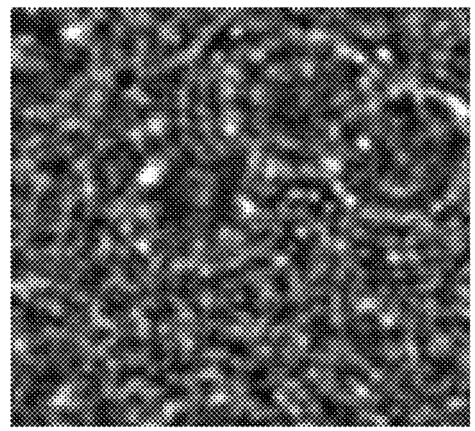
FIG. 5B is an input thumbnail used during neural network training.
Figure 5C:
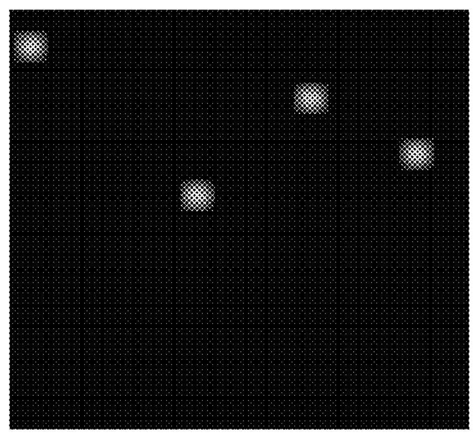
FIG. 5C is an output thumbnail used during neural network training.

The convolutional neural network has been the subject of training, considering 1000 input thumbnails, each input thumbnail having a size of 121×121 pixels. The input thumbnails were taken at random from a hologram image. An input thumbnail of this kind is shown in FIG. 5B. For each input thumbnail, an output thumbnail was determined by an expert. The output thumbnail shows the localization of the microorganisms. An example of an output thumbnail is shown in FIG. 5C. Training made it possible to parameterize the neural network.

Figure 6A:
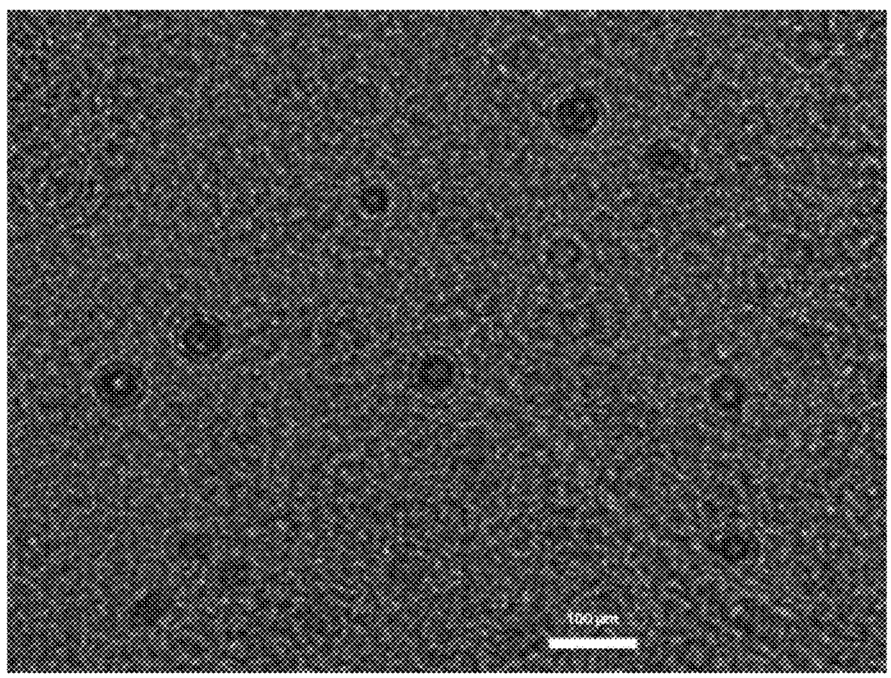
FIG. 6A is an image comprising diffraction patterns.
Figure 6B:
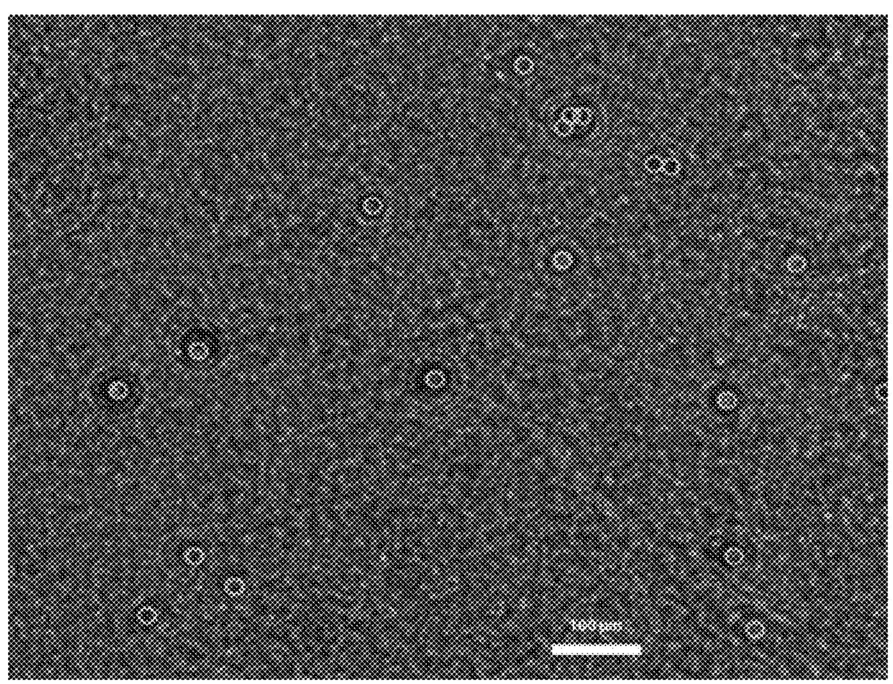
FIG. 6B represents detection of diffraction patterns from the image in FIG. 6A.

Following training, the neural network was used for detecting colonies of microorganisms automatically. FIG. 6A is an example of an image acquired by the image sensor. Each diffraction pattern corresponds to colonies of bacteria of the *Escherichia coli* type. FIG. 6B shows automatic detection of the colonies, each colony detected being represented by an open circle. Thus, the use of a neural network allows for detection, and counting, as well as localization, of colonies, moreover at an early stage of development.

Furthermore, by carrying out training on different species of microorganisms, employment of a neural network may allow for detection, counting and identification of the microorganisms.

The invention may be used for carrying out checking and counting of bacteria, as an aid in medical diagnostics, or in the field of environmental monitoring, or else control of industrial processes, for example in the field of food processing or cosmetics.

The invention claimed is:

1. A method for observation of a sample, the sample comprising colonies of microorganisms introduced into an opaque culture medium, the culture medium comprising nutrients allowing development of the microorganisms, the sample being arranged between a light source and an image sensor, the method comprising:

a) illuminating the sample with the light source, the light source emitting an incident light wave propagating along an axis of propagation;

b) acquiring an image of the sample by the image sensor; and c) from the image acquired, detecting microorganisms; wherein:

the culture medium extends, parallel to the axis of propagation, to a thickness of less than 500 μm;

the culture medium extends between an upper face and a lower face, perpendicular or sensibly perpendicular to the axis of propagation; and as they develop, the microorganisms form colonies, at least one colony forming a light channel extending from the upper face to the lower face through the culture medium, so that light propagates through the light channel to the image sensor and forms a light spot on the image acquired by the image sensor having an intensity greater than an intensity of an area on the image sensor corresponding to the culture medium.

2. The method according to claim 1, wherein the culture medium extends, parallel to the axis of propagation, to a thickness of less than 250 μm.

3. The method according to claim 1, comprising:

counting light spots formed on the image acquired by the image sensor; and estimating a number of colonies in the sample, as a function of a number of light spots counted on the image.

4. The method according to claim 1, comprising:

performing a morphological analysis of at least one light spot formed on the image acquired by the image sensor; and identifying the colony that produced the light spot, based on the morphological analysis.

5. The method according to claim 1, comprising:

acquiring a first image, at a first time point, the image comprising at least one diffraction pattern associated with a colony of microorganisms; and acquiring a second image, at a second time point, subsequent to the first time point, the second image comprising at least one light spot associated with the colony of microorganisms.

6. The method according to claim 1, wherein:

the culture medium extends in a confinement chamber;

the culture medium extends between two opposite faces, perpendicular or approximately perpendicular to the axis of propagation; and the confinement chamber is in contact with the culture medium at the level of the two opposite faces.

7. The method according to claim 1, wherein no image-forming lens is arranged between the sample and the image sensor.

8. The method according to claim 1 wherein:

an image-forming optical system is arranged between the sample and the image sensor, the optical system defining an object plane and an image plane; and the image sensor defines a detection plane;

wherein during image acquisition, at least one of:

the sample is shifted relative to the object plane by an object defocusing distance; and the detection plane is shifted, relative to the image plane, by an image defocusing distance.

9. The method according to claim 1, wherein an image-forming optical system is arranged between the sample and the image sensor, the optical system defining an object plane and an image plane; and the image sensor defines a detection plane;

wherein during image acquisition, the lower face of the sample corresponds to the object plane and the detection plane corresponds to the image plane.

10. The method according to claim 1, wherein the microorganisms are not stained.

11. The method according to claim 1, wherein the culture medium extends, parallel to the axis of propagation, to a thickness of less than 100 μm.

12. A method for observation of a sample, the sample comprising colonies of microorganisms introduced into an opaque culture medium, the culture medium comprising nutrients allowing development of the microorganisms, the sample being arranged between a light source and an image sensor, the method comprising:

a) illuminating the sample with the light source, the light source emitting an incident light wave propagating along an axis of propagation;

b) acquiring an image of the sample using the image sensor; and c) detecting microorganisms using the image;

wherein:

the culture medium comprises an upper face and a lower face extending in a direction crossing to the axis of propagation; and the microorganisms form at least one colony extending through the culture medium from the upper face to the lower face allowing light to propagate to the image sensor to form a light spot on the image sensor having an intensity greater than an intensity of an area on the image sensor corresponding to the culture medium.

13. The method according to claim 12, wherein the culture medium extends, parallel to the axis of propagation, to a thickness of less than 500 μm.

14. The method according to claim 12, wherein the culture medium extends, parallel to the axis of propagation, to a thickness sufficient to allow the at least one colony to extend from the upper face to the lower face.

15. The method according to claim 12, comprising:

counting light spots formed on the image acquired by the image sensor; and estimating a number of colonies in the sample, as a function of a number of light spots counted on the image.

16. The method according to claim 12, comprising:

performing a morphological analysis of at least one light spot formed on the image acquired by the image sensor; and identifying the colony that produced the light spot, based on the morphological analysis.

17. The method according to claim 12, comprising:

acquiring a first image, at a first time point, the image comprising at least one diffraction pattern associated with a colony of microorganisms; and acquiring a second image, at a second time point, subsequent to the first time point, the second image comprising at least one light spot associated with the colony of microorganisms.

18. The method according to claim 12, comprising: disposing the culture medium in a confinement chamber.

19. The method according to claim 12, comprising: the at least one colony forming a light channel; and propagating the light through the channel to the image sensor.

20. A method for observation of a sample, the sample comprising colonies of microorganisms introduced into a culture medium, the culture medium comprising nutrients allowing development of the microorganisms, the sample being arranged between a light source and an image sensor, the method comprising:

a) illuminating the sample with the light source, the light source emitting an incident light wave propagating along an axis of propagation;

b) acquiring an image of the sample using the image sensor; and c) detecting microorganisms using the image;

wherein:

the culture medium comprises an upper face and a lower face extending in a direction crossing to the axis of propagation; and the microorganisms form at least one colony comprising a channel through the culture medium from the upper face to the lower face allowing light to propagate through the channel to the image sensor at a higher intensity than light transmitted through the culture medium.

21. The method according to claim 20, wherein the culture medium is opaque.

* * * * *